(12) United States Patent
Harvey et al.

(10) Patent No.: US 10,131,786 B2
(45) Date of Patent: Nov. 20, 2018

(54) POLY((LACTIC-CO-GLYCOLIC ACID)-B-LYSINE) AND PROCESS FOR SYNTHESIZING A BLOCK COPOLYMER OF PLGA {POLY(LACTIC-CO-GLYCOLIC ACID)} AND PLL (POLY-ε-CBZ-L-LYSINE)

(75) Inventors: John Harvey, Upton, MA (US); Daniel Siegwart, Cambridge, MA (US); Heng Lian Huang, Roxbury Crossing, MA (US); Brian Hess, Charlestown, MA (US); Alex Aimetti, Waltham, MA (US)

(73) Assignees: INVIVO THERAPEUTICS CORPORATION, Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 429 days.

(21) Appl. No.: 14/232,525

(22) PCT Filed: Jul. 13, 2012

(86) PCT No.: PCT/US2012/046687
§ 371 (c)(1),
(2), (4) Date: Feb. 27, 2015

(87) PCT Pub. No.: WO2013/010087
PCT Pub. Date: Jan. 17, 2013

(65) Prior Publication Data
US 2015/0166786 A1 Jun. 18, 2015

Related U.S. Application Data

(60) Provisional application No. 61/507,505, filed on Jul. 13, 2011.

(51) Int. Cl.
| | | |
|---|---|---|
| C08G 81/00 | (2006.01) | |
| C08L 67/08 | (2006.01) | |
| A61K 47/42 | (2017.01) | |
| C08G 63/08 | (2006.01) | |
| C08L 101/16 | (2006.01) | |
| C08G 69/08 | (2006.01) | |
| C08G 69/10 | (2006.01) | |
| C08G 69/48 | (2006.01) | |
| C08L 77/04 | (2006.01) | |
| A61K 47/34 | (2017.01) | |

(52) U.S. Cl.
CPC .............. *C08L 67/08* (2013.01); *A61K 47/34* (2013.01); *A61K 47/42* (2013.01); *C08G 63/08* (2013.01); *C08G 69/08* (2013.01); *C08G 69/10* (2013.01); *C08G 69/48* (2013.01); *C08G 81/00* (2013.01); *C08L 77/04* (2013.01); *C08L 101/16* (2013.01); *C08L 2203/02* (2013.01)

(58) Field of Classification Search
None
See application file for complete search history.

(56) References Cited

U.S. PATENT DOCUMENTS

2010/0196481 A1   8/2010   Pritchard et al.

FOREIGN PATENT DOCUMENTS

| WO | 2006041613 A2 | 4/2006 |
|---|---|---|
| WO | 2010008792 A1 | 1/2010 |

OTHER PUBLICATIONS

Ji Hoon Jeong, et al.,Synthesis and characterization of poly(L-(lsine)-g-poly(D,L-lactic-co-glycolic acid) biodegradable micelles, Journal of Biomaterials Science, Polymer Edition, VSP. Jan. 2003, 11 pp., vol. 14, No. 1, Utrecht, NL.
Erin B. Lavik, et al., A Simple Synthetic Route to the Formation of a Block Copolymer of Poly(latic-co-glycolic acid) and Polylysine for the Fabrication of Functionalized, Degradable Structures for Biomedical Applications, Journal of Biomedical Materials Research, Jan. 10, 2001, pp. 291-294, vol. 58, No. 3, Wiley, New York, NY.
International Search Report, PCT/US2012/046687, dated Oct. 24, 2012, 3 pp.
International Report on Patentability for International Patent Application No. PCT/US2012/046687, dated Jan. 23, 2014, 8 pages.
International Search Report and Written Opinion for International Patent Application No. PCT/US2012/046687, dated Oct. 31, 2012, 10 pages.
European Office Action for European Patent Application No. 12738696.9, dated Nov. 28, 2014, 5 pages.
Taiwanese Office Action and Search Report for Taiwanese Patent Application No. 101125126, dated Apr. 16, 2014.

*Primary Examiner* — Ana L. Woodward
(74) *Attorney, Agent, or Firm* — Pierce Atwood LLP; Raymond G. Arner (57) ABSTRACT

A method of synthesizing copolymers is provided. The method can include coupling a degradable polymer to a poly(amino acid) and then deprotecting the copolymer if the poly(amino acid) contains protected side chains. Copolymer compositions are provided. These compositions include PLGA-PLL copolymers, PLGA-PLL-cbz copolymers, and copolymers of a polyester with a carboxylic acid end group coupled to a poly(amino acid) with an amine group. The compositions may include therapeutic blends and formulations of copolymers.

3 Claims, 4 Drawing Sheets

POLY((LACTIC-CO-GLYCOLIC ACID)-B-LYSINE) AND PROCESS FOR SYNTHESIZING A BLOCK COPOLYMER OF PLGA {POLY(LACTIC-CO-GLYCOLIC ACID)} AND PLL (POLY-ε-CBZ-L-LYSINE)

CROSS REFERENCE TO RELATED APPLICATIONS

This application is a U.S. National Stage of PCT International Application No. PCT/US2012/046687, which was filed on Jul. 13, 2012, which claims the benefit of U.S. provisional patent application No. 61/507,505, which was filed Jul. 13, 2011, the entire contents of which are incorporated herein by reference.

FIELD OF INVENTION

The disclosure herein relates to the synthesis of block and graft copolymers.

BACKGROUND

A copolymer is a polymer derived from two or more monomeric species. Copolymers can be classified based on how the copolymer constituent units are arranged along the chain, including block copolymers and graft copolymers. Block copolymers comprise two or more homopolymer subunits linked by covalent bonds. Graft polymers are a branched copolymer in which the side chains are structurally distinct from the main chain.

SUMMARY

In an aspect, the invention relates to a method of synthesizing a block or graft copolymer comprising coupling a degradable polymer to a poly(amino acid) by combining the degradable polymer, the poly(amino acid), a solvent, and a coupling catalyst to form a copolymer solution and isolating the copolymer by dialysis of the copolymer solution in water.

In an aspect, the invention relates to a composition produced by coupling a degradable polymer to a poly(amino acid) by combining the degradable polymer, the poly(amino acid), a solvent, and a coupling catalyst to form a copolymer solution and isolating the copolymer by dialysis of the copolymer solution in water.

In an aspect, the invention relates to a composition produced by coupling a degradable polymer to a poly(amino acid) containing protected side chains by combining the degradable polymer, the poly(amino acid), a solvent, and a coupling catalyst to form a copolymer solution and isolating the copolymer by dialysis of the copolymer solution in water and deprotecting the isolated copolymer by DCM thin film.

In an aspect, the invention relates to a composition produced by coupling a degradable polymer to a poly(amino acid) by combining the degradable polymer, the poly(amino acid), a solvent, and a coupling catalyst to form a copolymer solution and isolating the copolymer by dialysis of the copolymer solution in water, and deprotecting the copolymer by DCM thin film if the poly(amino acid) contains protected side chains, wherein the method further includes at least one of the coupling catalyst being DCC/DMAP/NHS, the solvent being DMSO, dialysis including a mixture of DMSO and ethanol, or drying the isolated copolymer by lyophillization.

In an aspect, the invention relates to a composition comprising a block copolymer of poly(lactic-co-glycolic acid) and poly(ε-carbobenzoxy-L-Lysine).

In an aspect, the invention relates to a composition comprising a block copolymer of poly(lactic-co-glycolic acid) and poly(L-Lysine).

In an aspect, the invention relates to a composition comprising a block or graft copolymer of a polyester with a carboxylic acid end group coupled to a poly(amino acid) with an amine group.

In an aspect, the invention relates to a composition comprising a blend of i) poly(lactic-co-glycolic acid) and, ii) a block copolymer of poly(lactic-co-glycolic acid) and poly(ε-carbobenzoxy-L-lysine).

In an aspect, the invention relates to a composition comprising a blend of i) poly(lactic-co-glycolic acid) and, ii) a block copolymer of poly(lactic-co-glycolic acid) and poly(L-lysine).

In an aspect, the invention relates to a composition comprising a blend of i) poly(lactic-co-glycolic acid) and, ii) a block copolymer of a polyester with a carboxylic acid end group coupled to a poly(amino acid) with an amine group.

In an aspect, the invention relates to a composition comprising a blend of i) poly(lactic-co-glycolic acid) and, ii) a graft copolymer of a polyester with a carboxylic acid end group coupled to a poly(amino acid) with an amine group.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENTS

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Embodiments include methods of synthesizing block or graft copolymers. In an embodiment, a method of synthesizing a block or graft copolymer may include coupling a degradable polymer to a poly(amino acid) to form a copolymer solution. As used herein "a degradable polymer" is one that contains degradable bonds (e.g. ester or amide) that are degradable at physiological conditions (e.g. in the body). As a test of degradation, the polymer may be placed into a PBS solution or serum at 37° C., and the extent of degradation may be monitored by measuring the identity and molecular weight of the degradation products. The degradable polymer may have a single carboxylic acid terminal group, including but not limited to poly(lactic-co-glycolic acid) (PLGA) with any weight ratio of lactide to glycolide, lactide to poly lactic acid, lactide to poly glycolic acid or lactide to poly($\varepsilon$-caprolactone). The degradable polymer may have a single acyl terminal end group, including but not limited to PLGA with any weight ratio of lactide to glycolide, lactide to poly lactic acid, lactide to poly glycolic acid or lactide to poly($\varepsilon$-caprolactone). The degradable polymer may be a polyester with a carboxylic acid end group. The poly(amino acid) may have an amine terminal end group. The poly(amino acid) may be poly(L-lysine) (PLL) or poly($\varepsilon$-carbobenzoxy-L-lysine) (PLL-cbz). In an embodiment, the molar equivalents of PLGA to PLL-cbz may be 1:1. In an embodiment, the molar equivalents of PLGA to PLL-cbz may be greater than 1:1, with removal of excess unreacted PLL-cbz, which may also yield a coupled block copolymer. In an embodiment, the reaction time may be 1-6 days at a temperature of 20-30° C. The reaction time may be any one value in the range of 1-6 days or in a range between any two values in the range of 1-6 days where the two values are selected from any two in the group of 1 day and every one hour time increase from 1 day to 6 days (i.e., the group of 1 day, 1 day plus 1 hour, 1 day plus two hours . . . 6 days). In an embodiment, the reaction time may be less than 1 day or longer than 6 days. In an embodiment, the deprotection reaction is 30 minutes, or 10-600 minutes, which may achieve complete deprotection. The deprotection reaction time may be any value in the range of 10-600 minutes, or in a range between any two values in the range of 10-600 minutes where the two values are selected from any two in the group of 10 minutes and every one minute increase from 10 minutes to 600 minutes. In an embodiment, the deprotection time is greater than 30 minutes.

In an embodiment, the method may include a coupling catalyst. The coupling catalyst may be any catalyst capable of coupling amines and carboxylic acids. The coupling catalyst may include but is not limited to DCC/DMAP, DCC/DMAP/NHS, EDC/DMAP, PyBOB, CDMT, HATU, TBTU, HBTU, HCTU, or DIC. In an embodiment, the coupling catalyst is DCC/DMAP/NHS. In an embodiment, the molar ratio of reactions may be PLGA:PLL-cbz:DCC:DMAP:NHS of 1:1:1.5:0.4:1.5 at a PLGA concentration range of 100-400 mg/mL or 0.003-0.015 M. The PLGA concentration may be any one value in the range of 100-400 mg/mL, or in a range between any two values in the range of 100-400 mg/mL where the two values are selected from any two in the group of 100 mg/mL and every ten mg/mL increase from 100 mg/mL-400 mg/mL. The PLGA concentration may be any one value in the range of 0.0001-0.03 M, or in a range between any two values in the range of 0.0001-0.03 M where the two values are selected from any two in the group of 0.0001 M and every one tenth of a molarity increase from 0.0001 M to 2.5 M.

In an embodiment, the method may include a solvent for coupling. The solvent may include but is not limited to DMSO, DMF, dichloromethane or chloroform. In an embodiment, the solvent is DMSO.

In an embodiment, the method may include reacting the dry starting materials in an inert atmosphere. An inert atmosphere may include nitrogen, argon, or helium. An inert atmosphere may be nitrogen, argon, or helium. In an embodiment, the method may include reacting the dry starting materials in ambient conditions under air.

In an embodiment, the method may include isolating the block or graft copolymer. Isolating the copolymer may include isolation by dialysis, precipitation, evaporation or flow filtration. In an embodiment, the method includes isolating the copolymer by dialysis in water. In an embodiment, the method includes isolating the copolymer by dialysis in a mixture including DMSO and ethanol. In an embodiment, the ratio of DMSO to ethanol is 1:0.5 by volume. In an embodiment, the ratio of DMSO to ethanol is 1:0-1.2:0.5

In an embodiment, the method may include deprotecting the copolymer if the poly(amino acid) contains protected side chains. For example, PLL-cbz contains cbz protected side chains. Other side chains may be used. The side chain refers to parts of the polymer that are not the backbone or the end groups. Deprotecting may include dissolving the copolymer in a deprotecting solvent and adding a deprotecting reagent. Deprotecting solvents may include but are not limited to dichloromethane and chloroform. Deprotecting agents may include hydrogen bromide solution (33% in glacial acetic acid), palladium on carbon or TFA/HCl. In an embodiment, deprotecting may include a homogeneous reaction using the DCM thin film method. The DCM thin film method may include a co-solvent range of 5-60 mL per 10 g PLGA-PLL-cbz. The co-solvent range may be any one value in the range of 5-60 mL per 10 g PLGA-PLL-cbz, or in a range between any two values in the range of 5-60 mL per 10 g PLGA-PLL-cbz. where the two values are selected from any two in the group of 5 mL per 10 g PLGA-PLL-cbz and every 1 mL increase from 5-60 mL per 10 g PLGA-PLL-cbz.

In an embodiment, the method includes isolating the deprotected copolymer. Isolating the deprotected copolymer may include but is not limited to precipitation, dialysis, flow filtration, evaporation, ion exchange, or purification. In an embodiment, isolating the deprotected copolymer includes dilution in a solvent followed by washing and precipitation.

Figure 1:
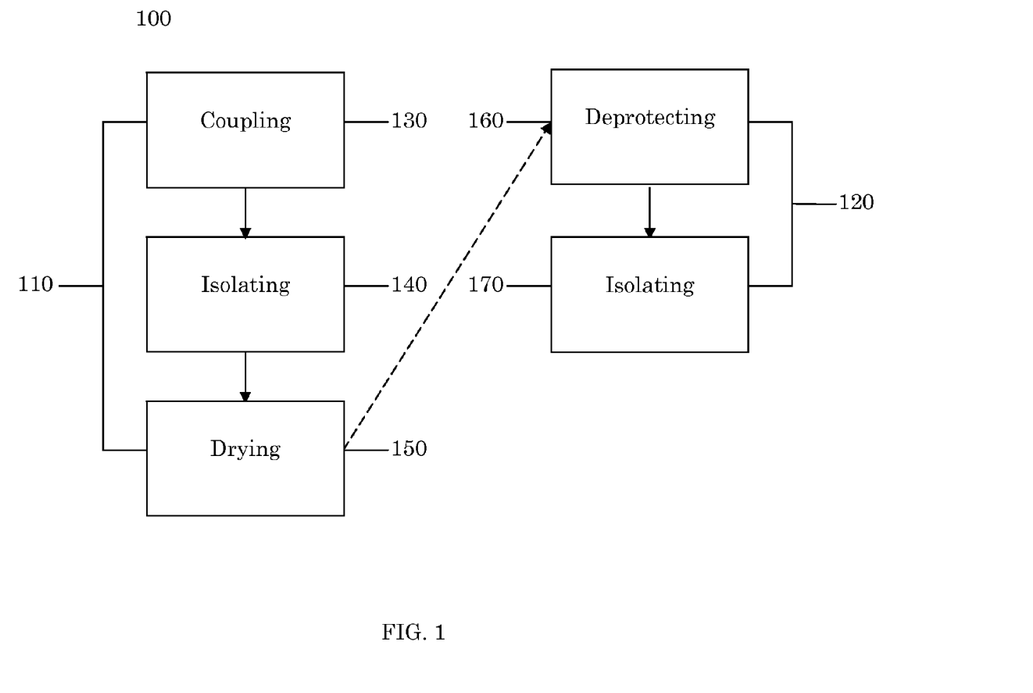
FIG. 1 illustrates an exemplary method of synthesizing a block or graft copolymer.

Referring to FIG. 1, an example method 100 of synthesizing a block or graft polymer is illustrated with a coupling step 110 including coupling 130, isolating 140 and drying 150. Method 100 may or may not include a deprotecting step 120 including deprotecting 160 and isolating 170.

The coupling step 110 of method 100 may include coupling reaction 130; coupling reaction 130 and isolating 140; or coupling reaction 130, isolating 140 and drying 150. Coupling reaction 130 may include coupling a degradable polymer to a poly(amino acid) with a coupling catalyst in a solution. Isolating 140 may include isolating the copolymer by dialysis, precipitation, evaporation or flow filtration. Drying 150 may include drying copolymer by lyophillization.

The deprotecting step 120 of method 100 may include deprotecting reaction 160; or deprotecting reaction 160 and isolating 170. The deprotecting step 120 may be desired if the poly(amino acid) contains protected side chains. Deprotecting reaction 160 may include dissolving the copolymer in a deprotecting solvent and adding a deprotecting agent. Isolating 170 may include isolating the deprotected copolymer by precipitation, dialysis, flow filtration, evaporation, or ion exchange purification.

In an embodiment, a method for synthesizing a block copolymer composed of PLGA and PLL-cbz is provided. In an embodiment, a method for synthesizing a block copolymer composed of PLGA and PLL is provided. Embodiments include methods of synthesizing and deprotecting the PLGA-PLL block copolymer. An example of how these methods may be conducted appears in FIG. 2.

Embodiments include methods for synthesizing a block or graft copolymer of a polyester with a carboxylic acid end group coupled to a poly(amino acid) with an amine end group (protected or non-protected side chains). An example of how these methods may be conducted appears in FIG. 2.

Figure 2:
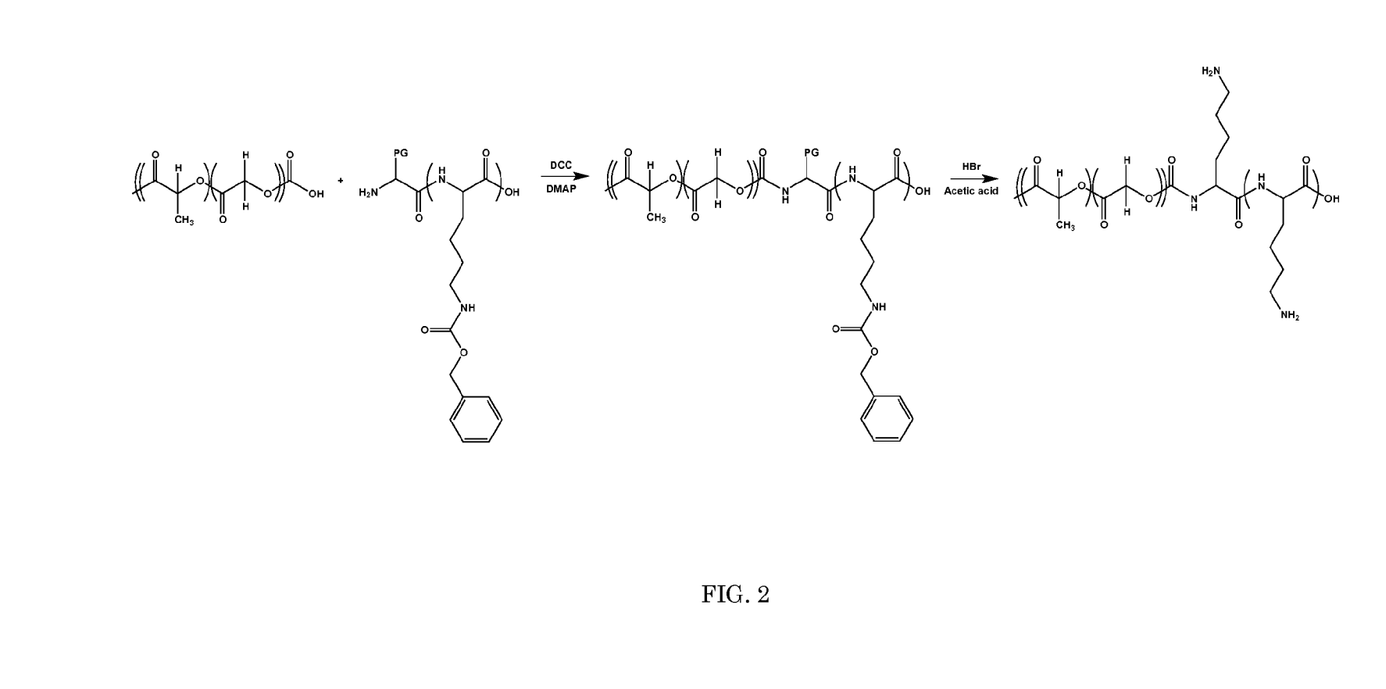
FIG. 2 illustrates an example of a synthetic route to prepare a block copolymer.

Referring to FIG. 2, an example of a synthetic route of preparing a block copolymer is illustrated.

Embodiments include compositions comprising the product of any of the above methods. Embodiments include a composition comprising a block copolymer of PLGA and PLL-cbz. Embodiments include compositions comprising a block copolymer of PLGA and PLL. Embodiments include compositions comprising a block copolymer of a polyester with a carboxylic acid end group coupled to a poly(amino acid) with an amine group. The amine end group may include protected or non-protected side chains.

Embodiments include compositions comprising a graft copolymer of a polyester with a carboxylic acid end group coupled to a poly(amino acid) with an amine group. The amine end group may include protected or non-protected side chains.

Figure 3:
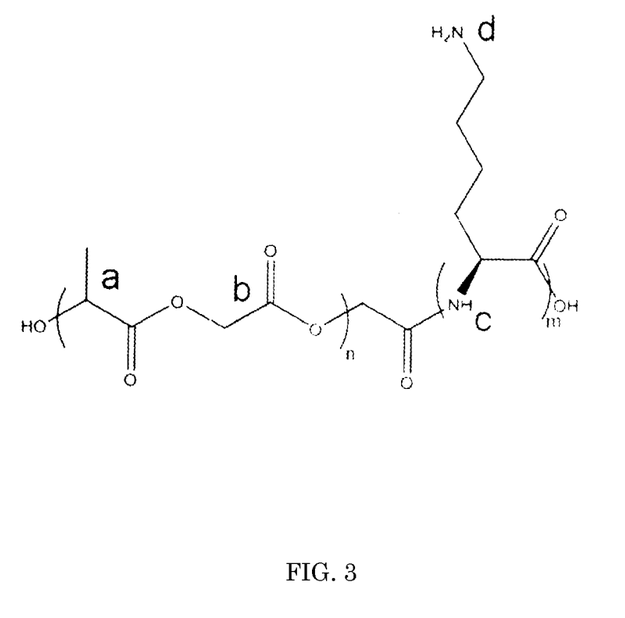
FIG. 3 illustrates a $^1$H NMR spectrum of purified block copolymer.
Figure 4:
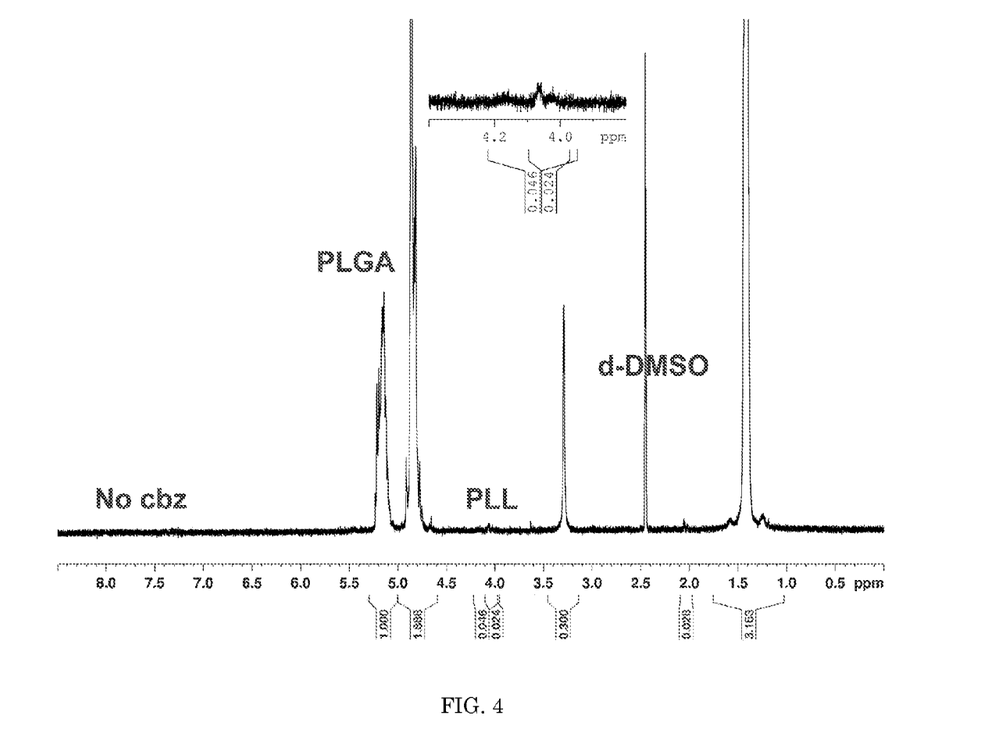
FIG. 4 illustrates the final structure of the block copolymer poly((lactic-co-glycolic acid)-b-lysine).

Referring to FIG. 3, the final structure of the block copolymer poly((lactic-co-glycolic acid)-b-lysine) is illustrated. Referring to FIG. 4, the $^1$H NMR spectrum of purified block copolymer, prepared by the method of Example 1, below, is illustrated. The spectrum shows successful conjugation of PLGA to PLL. The spectrum contains no peaks for cbz, indicating complete deprotection. Further, the spectrum shows no residual solvents or impurities are present. The NMR solvent was d-DMSO, 128 scans, 500 MHz.

Embodiments include compositions comprising a block copolymer of PLGA and PLL-cbz with or without at least one of cells or one or more therapeutic agent for therapeutic implantation in the central nervous system or other medically relevant anatomic site. Embodiments include compositions comprising a block copolymer of PLGA and PLL with or without at least one of cells or one or more therapeutic agent for therapeutic implantation in the central nervous system or other medically relevant anatomic site.

Embodiments include compositions comprising a block copolymer of a polyester with a carboxylic acid end group coupled to a poly(amino acid) with an amine group with or without at least one of cells or one or more therapeutic agent for therapeutic implantation in the central nervous system or other medically relevant anatomic site. Embodiments include compositions comprising a graft copolymer of a polyester with a carboxylic acid end group coupled to a poly(amino acid) with an amine group with or without at least one of cells or one or more therapeutic agent for therapeutic implantation in the central nervous system or other medically relevant anatomic site.

Embodiments include compositions comprising a blend of PLGA and a block copolymer of PLGA and PLL-cbz with or without at least one of cells or one or more therapeutic agent for therapeutic implantation in the central nervous system or other medically relevant anatomic site. Embodiments include compositions comprising a blend of PLGA and a block copolymer of PLGA and PLL with or without at least one of cells or one or more therapeutic agent for therapeutic implantation in the central nervous system or other medically relevant anatomic site. Embodiments include compositions comprising a blend of PLGA and a block copolymer of a polyester with a carboxylic acid end group coupled to a poly(amino acid) with an amine group with at least one of cells or one or more therapeutic agent for therapeutic implantation in the central nervous system or other medically relevant anatomic site. Embodiments include compositions comprising a blend of PLGA and a graft copolymer of a polyester with a carboxylic acid end group coupled to a poly(amino acid) with an amine group at least one of cells or one or more therapeutic agent for therapeutic implantation in the central nervous system or any medically relevant anatomic site. Medically relevant anatomic sites may include but are not limited to the central nervous system, the peripheral nervous system, organs, intra peritoneal and the musculoskeletal system. A medically relevant anatomic site may be in the spinal cord. A medically relevant site may be a site of injury in the central nervous system, the peripheral nervous system, organs, intra peritoneal, or the musculoskeletal system.

Cells may include but are not limited to somatic cells, stem cells, neural stem cells, precursor cells, and induced pluripotent stems cells. Therapeutic agents may include but are not limited to steroids, enzymes, anti-inflammatories, oncolytics, growth factors, antibodies, anesthetics, peptides, proteins, methylprednisolone, prodrugs of methylprednisolone, pharmaceutically acceptable salts of methylprednisolone, dexamethasone, prodrugs of dexamethasone, pharmaceutically acceptable salts of dexamethasone, inhibitors of NOS or NO production, pharmaceutically acceptable salts or inhibitors of NOS or NO production, antioxidants, pharmaceutically acceptable salts of antioxidants, spin traps, pharmaceutically acceptable salts of spin traps, peroxy nitrite scavengers, or pharmaceutically acceptable salts of nitrite scavengers. Additional examples of therapeutic agents may be found in U.S. Patent Publication US2010/0196481, which is incorporated herein by reference as if fully set forth. Methods of implementing a block or graft copolymer listed herein or made by a method herein may be arrived at by using the block or graft copolymer listed herein or made by a method herein in a method described in US2010/0196481.

Embodiments include methods of treating a patient. Methods of treating a patient may include implanting any composition contained herein at a medically relevant anatomic site. Medically relevant anatomic sites may include the central nervous system, the peripheral nervous system, organs, intra peritoneal, and the musculoskeletal system. A medically relevant anatomic site may be in the spinal cord. A medically relevant site may be a site of injury in the central nervous system, the peripheral nervous system, organs, intra peritoneal, or the musculoskeletal system. Compositions herein may further include at least one of porous scaffolds, microparticles, nanoparticles or micelles. Methods of implantation may include surgical methods, with implantation following myletomy or minimally invasive (in the case of micro/nanoparticles) intraspinal/intrathecal injection.

Methods described herein may improve block copolymer functionality by increasing the percentage of PLL conjugation to PLGA. Methods herein may improve the manufacturability and scale of manufacture for the block copolymer. Methods herein may improve the consistency of manufacturing. Methods herein may improve biocompatibility by limiting residual solvent contamination, making the resulting block copolymer appropriate for therapeutic implantation within the spinal cord, CNS and/or other medically relevant anatomic sites. Methods herein may result in a block copolymer that can be formulated in combination with cells and/or therapeutic agents for therapeutic implantation in the CNS or other medically relevant anatomic sites. A final product may be a conjugated copolymer mixture with PLGA, with no residual unreacted PLL.

EMBODIMENTS

The following list includes particular embodiments of the present invention. The list, however, is not limiting and does not exclude alternate embodiments, as would be appreciated by one of ordinary skill in the art.

1. A method of synthesizing a block or graft copolymer comprising: coupling a degradable polymer to a poly(amino acid) using a coupling catalyst in a solvent.
2. The method of embodiment 1, further comprising isolating the copolymer.
3. The method of embodiment 2, further comprising drying the copolymer.
4. The method of any one or more of the preceding embodiments further comprising deprotecting the copolymer if the poly(amino acid) contains protected side chains.
5. The method of embodiment 4 further comprising isolating the deprotected copolymer.
6. The method of any one or more of the preceding embodiments, wherein the degradable polymer has a single carboxylic acid terminal group.
7. The method of any one or more of the preceding embodiments, wherein the degradable polymer has a single acyl terminal end group.
8. The method of any one or more of the preceding embodiments, wherein the degradable polymer is PLGA.
9. The method of any one or more of the preceding embodiments, wherein the degradable polymer is PLGA with any weight ratio of lactide to glycolide, poly lactic acid, poly glycolic acid, or poly(ε-caprolactone).
10. The method of any one or more of the preceding embodiments, wherein the degradable polymer is a polyester with a carboxylic acid end group.
11. The method of any one or more of the preceding embodiments, wherein the poly(amino acid) has an amine terminal end group.
12. The method of any one or more of the preceding embodiments, wherein the poly(amino acid) is PLL.
13. The method of any one or more of the preceding embodiments, wherein the poly(amino acid) is PLL-cbz.
14. The method of any one or more of the preceding embodiments, wherein the coupling catalyst is DCC/DMAP, DCC/DMAP/NHS, EDC/DMAP, Pyob, CDMT, or HATU.
15. The method of any one or more of the preceding embodiments, wherein the coupling catalyst is DCC/DMAP/NHS.
16. The method of any one or more of the preceding embodiments, wherein the solvent is DMSO, DMF, dichloromethane, or chloroform.
17. The method of any one or more of the preceding embodiments, wherein the solvent is DMSO.
18. The method of any one or more of the preceding embodiments, wherein isolating the copolymer includes dialysis in water or a combination of DMSO and ethanol.
19. The method of embodiment 18, wherein the water includes a mixture of DMSO and ethanol.
20. The method of any one or more of the preceding embodiments further comprising drying the copolymer by lyophilization.
21. The method of any one or more of the preceding embodiments further comprising deprotecting the copolymer by DCM thin film.
22. The method of any one or more of the preceding embodiments, wherein isolating the deprotected copolymer includes purification by dilution in an isolating solvent followed by precipitation and washing.
23. A composition comprising a product of the method of any one or more of the preceding embodiments.
24. A composition comprising a block copolymer of PLGA and PLL-cbz.
25. A composition comprising a block copolymer of PLGA and PLL.
26. A composition comprising a block copolymer of a polyester with a carboxylic end group coupled to a poly (amino acid) with an amine group.
27. A composition comprising the composition of any one or more of embodiments 23-26 and cells.
28. The composition of embodiment 27, wherein the cells are stem cells or neural stem cells.
29. A composition comprising the composition of any one or more of embodiments 23-28 and one or more therapeutic agent.
30. The composition of embodiment 29, wherein the therapeutic agent is a steroid, an enzyme, an anti-inflammatory, an oncolytic, growth factors, antibodies, anesthetics, peptides, proteins, methylprednisolone, prodrugs of methylprednisolone, pharmaceutically acceptable salts of methylprednisolone, dexamethasone, prodrugs of dexamethasone, pharmaceutically acceptable salts of dexamethasone, inhibitors of NOS or NO production, pharmaceutically acceptable salts or inhibitors of NOS or NO production, antioxidants, pharmaceutically acceptable salts of antioxidants, spin traps, pharmaceutically acceptable salts of spin traps, peroxy nitrite scavengers, or pharmaceutically acceptable salts of peroxy nitrite scavengers.
31. A composition comprising the composition of any of embodiments 23-30 for therapeutic implantation at any medically relevant anatomic site.
32. A composition comprising the composition of any of embodiments 23-30 for therapeutic implantation in the central nervous system, the peripheral nervous system, organs, intra peritoneal or the musculoskeletal system.
33. A method of treatment including implanting the composition of any of embodiments 23-30 at any medically relevant anatomic site.
34. A method of treatment including implanting the composition of any of embodiments 23-30 in the central nervous system, the peripheral nervous system, organs, intra peritoneal or the musculoskeletal system.

EXAMPLES

The following non-limiting examples are provided to illustrate particular embodiments.

Example 1

A 10 gram PLGA-PLL scale reaction will be used as an example for explaining chemical and solvent volumes used in this process. This is a non-limiting example and the reaction scale can be adapted using the chemical and solvent volume examples provided.

Materials. The following materials were used to synthesize the PLGA-PLL bock copolymer. These materials are listed as a non-limiting example and adaptations in the following materials may still result in the formation of the described block copolymer. For example, PLGA and PLL-cbz of different molecular weights could be used. Also, different catalysts could be used to couple the block copolymers together such as DCC/DMAP, EDC/DMAP, PyBOB, CDMT, HATU, DIC, HBTU, or HCTU.

Substances and implements. Poly(lactic-co-glycolic acid) (PLGA) [MW=24,000-38,000, IV=0.32-44 dl/g (Evonik, Resomer RG 503 H)], poly-ε-Cbz-L-lysine (PLL-cbz) [MW=500-4,000 (Sigma Aldrich, P4510)], N,N'-Dicyclohexylcarbodiimide (DCC) [99% (Sigma-Aldrich, D80002)], hydroxysuccinimide (NHS) (Alfa Aesar, A10312), 4-dimethylaminopyridine (DMAP) [Puriss Grade, (Sigma-Aldrich, 29224)], dimethyl sulfoxide (DMSO) anhydrous (Alfa Aesar, 43998), hydrogen bromide solution 33% w/v in acetic acid (Sigma-Aldrich, 18735), glacial acetic acid (Alfa Aesar, 36289), dichloromethane (DCM) [anhydrous, ≥99.8% (Sigma-Aldrich, 270997)], sodium bicarbonate (BDH, BDH0280), ethanol (EMD, EX0276-3), distilled water (Macro Chemicals, H453-09), dialysis membrane [MWCO 12-14,000, Spectra/Por 4, (Spectrum Labs, 132709)], Kimwipes™ (VWR, 82003-820), rubber bands (Alliance, 42339), spatula [8" (VWR, 80027-503 or equivalent)], liquid nitrogen (Airgas or equivalent), 60 mL, 20 mL luer lock and luer slip syringes (HSW, Air-Tite: AL50, A50, AL20), 0.22 μm syringe filters (VWR, 28143-878), 40 mL glass vials (Wheaton, 225315), 178 ml glass jar (VWR, 89045-780), 14 gauge×6" Teflon™ pipetting needles (Hamilton 90664), 16 gauge×6" pipetting needles blunt end (Cadence, 9873), 16 gauge 1½" needle (BD, 305198), 2 L, 0.5 L beakers (VWR, 89000-216, 8900-212), 50 μm nylon mesh (Biodesign Inc., N50S), 200 mL Schlenk Flask (Chemglass, AF-0528-04), stir bars 1", 1½", 2½", (VWR, 58949-094, 58949-119, 58947-172), rubber septum stopper, (VWR, 89097-558), 250 mL polypropylene bottles (Beckman Coulter, 356011)), 250 mL round bottom flask (Chemglass, CG-1506), Buchner funnel with rubber adaptor (Chemglass, CG-1888-05), Filter flask (Chemglass, CG-1550), and Parafilm™ (VWR, 52858-000).

Equipment. Schlenk Line vacuum manifold with argon source (Chemglass, AF-0060-02; LeyboldTrivac, TRIVAC B), centrifuge (Beckman Coulter, Allegra X-22), Standard mini vortex (VWR, 58816-121), lyophillizer (VirTis, BTK4ZL-105), stir plate (Chemglass, CGS 1990-10K), rotary evaporator (Rotovap) with vacuum pump (BUCHI R-124, BUCHI V-700), liquid nitrogen dewar (VWR, Cryopro L-5), freezer −20° C. (VWR 47747-222 or equivalent), fume hoods (Kewaunee Scientific, Supreme Air Fume Hood or equivalent), analytical balances (Mettler Toledo, AT-20; AE-240), vacuum pump (Gast, DAA-V716A-EB), and timer (VWR, 33501-418).

Procedure. Preparations: the initial conjugation reaction between PLGA and PLL-cbz is moisture-sensitive. To enable high conjugation efficiency, the starting materials were dried under vacuum for >30 minutes. The reaction flask was then back-filled with an inert gas (e.g. nitrogen or argon) and the reaction was conducted under an inert atmosphere without water or oxygen. Also, an anhydrous solvent was used. PLGA and PLL-cbz powder (stored in −20° C. freezer) were warmed to room temperature by placing them in a desiccator for approximately 2 hrs. prior to processing.

Conjugation Step:
1. A 1½" bar was placed in a 200 mL Schlenk flask. 10.0 g PLGA, 726.0 mg PLL-cbz, 100.0 mg DCC, 16.0 mg DMAP, and 56.0 mg NHS was weighed and placed in the flask.
2. The top of the flask was sealed with a rubber septum stopper; the sidearm of the flask was connected to the vacuum manifold in the fume hood.
3. The flask was attached to the Schlenk line vacuum and dried for 30 minutes.
4. The vacuum line was shut off and the argon pressured line was slowly opened to fill the flask with argon.
5. 2×15.0 mL (30.0 mL total) anhydrous DMSO was added using a 20 mL syringe to dissolve the starting materials and catalysts.
6. The plate stirrer was turned on to a set point of 500 rpm.
7. The solution was allowed to homogenize and react for 48 hours.
8. After 48 hours, the rubber septum stopper was removed from the Schlenk flask; the solution was diluted with 60.0 mL of DMSO.
9. 25 mL of polymer solution was loaded into each of four 25 mL syringes. The solution was filtered from each syringe through 0.22 um filters into clean 40 mL glass vials.
10. 50.0 mL ethanol was added to the filtered polymer solution and mix until no precipitate was observed.
11. The ethanol-DMSO-polymer solution was added into three Spectra/Por 4 Dialysis membranes (MWCO 12,000-14,000) cut to approximately 5 inches. Both ends of the tubes were clipped (sealed off).
12. The dialysis bags filled with the polymer solution were placed into a beaker filled with 2.0 L of distilled water and a 2½" stir bar was added.
13. The stir plate was turned on and set the speed to 200 rpm. The polymer solution was dialyzed for one day with four changes of water (4×2.0 L, waiting 2 hr, 2 hr, overnight, and 4 hr between changes). The final product in the dialysis bags was comprised of white powder and water.
14. The powder and the solution were transferred into a centrifuge tube; the mixture was centrifuged at 4200 rpm for 20 minutes. The supernatant was removed and the polymer at the bottom was collected with a spatula. The polymer was transferred into a 178 mL glass jar; 10 mL of distilled water was added and the mixture was vortexed for approximately 1 minute.
15. The cloudy supernatant was transferred into 250 mL polypropylene bottles and the liquid was centrifuged at 4200 rpm for 2 hours to recover any fine conjugated polymer on the bottom of the bottle. All the powder was collected in a pre-weighed (and recorded) clean 178 mL glass jar.
16. 1 piece of Kimwipe™ was placed on top of the jar and was secured with a rubber band. The tubes were placed in a dewar flask filled with liquid nitrogen, and frozen for 10 minutes.
17. The lyophilizer (ambient, condenser on ~−104° C., Vacuum ~6-10 mT) was started and the polymer was allowed to dry for at least 48 hours. This step was complete when a dried white powder was observed.
18. After lyophilization was complete, the glass jar containing the polymer was weighed and recorded. The polymer yield was determined by subtracting the weight of the glass jar in step 15 from the weight of the jar plus polymer.
19. If not proceeding immediately to deprotection, the polymer was purged under argon for 2-3 minutes, and the cap firmly attached. The closure was sealed with Parafilm™ and the polymer was stored at −20° C.

Deprotection and Processing Step:
20. The dry conjugated polymer was placed in a 250 mL round bottom flask equipped with a 1½" stir bar. The weight of the flask with the powder was weighed and recorded.
21. 60.0 mL dichloromethane was added to dissolve the polymer powder and s stir plate was set to 400 rpm. It was stirred for approximately one hour until a clear, homogeneous solution was observed.

22. The round bottom flask was attached to the rotavap, the condition was set to 100 mmHg, water bath temp to 28-30° C., and rotator to 100 rpm. This removed most of the dichloromethane and resulted in a "thin film" after approximately 10-15 minutes.
23. The weight of the flask with the "thin film" was weighed and recorded.
24. The weight of step 20 was subtracted from the weight of step 23 to get the weight of DCM. The weight of the DCM was divided by its density to give the volume of DCM in the thin film. It should be within the range of 15.0±1.0 mL of DCM per 9-10 g of conjugated polymer.
25. The thin film was dissolved with 5.0 mL hydrogen bromide solution. The stir plate was set to stir at 400 rpm, the flask was rotated about 10-15 times so the acid touched the entire film and the polymer was dissolved completely. The top was covered with a rubber septum stopper. The rotations were repeated 5-6 times approximately every 5 minutes. It was stirred for 30 minutes.
26. 20 mL glacial acetic acid was added to dilute the yellow solution. The stir bar was removed with a magnetic retriever. The solution was rotavapped with the following conditions: 50 mmHg, water bath temp 27-30° C., rotation at 200 rpm for 10 minutes. The solution in the flask became thicker and more viscous.
27. The solution was aspirated into a 60 mL syringe adapted with a 14 gauge×6" blunt Teflon™ needle to measure the volume. Based on the polymer yield determined in step 18, sufficient glacial acetic acid was added to dilute the solution to yield a final concentration of 230 mg/mL. The solution was stirred on a stir plate to homogenize for about 2-3 minutes. Note: The final concentration of polymer to acid should be 230 mg/mL, e.g. 9.2 g of conjugated powder should yield a final volume of 40 mL in acetic acid.
28. 1.9 L of 1:1 water/ethanol (v:v) solution was prepared in a 2 L beaker.
29. The polymer solution was loaded into a 60 mL syringe adapted with a16 gauge×1½" needle. It was precipitated by injecting the acid solution as a slow, continuous stream into the 1:1 water/ethanol solution, stirring at 800 rpm with a 2½" stir bar.
30. Once the polymer solution was ejected from the syringe, the precipitation mixture stirred for 10 minutes.
31. The ethanol/water/polymer solution was carefully poured through the 50 μm nylon mesh to remove the solvents and collect the polymer in a Buchner funnel adapted to a filter flask. Vacuum was applied to the Buchner flask and dried the polymer in the nylon mesh for approximately 3 minutes.
32. The nylon mesh with vacuum dried polymer was transferred to a 0.5 L beaker. 500.0 mL of distilled water was added. The stir plate adapted with 1½" stir bar was set to 600 rpm for 30 min. The polymer was vacuum dried as in step 31.
33. The nylon mesh bag with vacuum dried polymer was transferred to a 0.5 L beaker. 500.0 mL of 0.5M sodium bicarbonate solution was added. The stir plate adapted with 1½" stir bar was set to 600 rpm for 30 min. The polymer was vacuum dried as in step 31.
34. The nylon mesh with dried polymer was transferred to a 0.5 L beaker. 500.0 mL of distilled water was added. The stir plate adapted with 2" stir bar was set to 600 rpm for 15 min. The polymer was vacuum dried as in step 31. This step, step 34, was repeated three times.
35. The polymer was transferred into two 178 mL glass jars. With the cap removed, 1 piece of Kimwipe™ was placed on top and secured with a rubber band. The jar was placed in a dewar filled with liquid nitrogen, and frozen for approximately 10 minutes.
36. The lyophilizer (ambient, condenser on ~-104° C., vacuum on ~6-10 mT) was started and allowed to run for at least 48 hours. The process was complete when a dried white powder was observed.

The polymer was purged under argon for 2-3 minutes, and the cap was firmly attached. The closure was sealed with parafilm and the polymer was stored at −20° C.

Results

Referring to Table 1 below, the table of results demonstrates that the process yields a final block copolymer with high conjugation and purity. Molecular weight (a) was calculated using gel permeation chromatography (GPC). Elemental analysis % (b) was calculated by elemental analysis. Conjugation efficiency % (c) was calculated by $^1$H NMR and elemental analysis.

TABLE 1

| Molecular weight (g/mol) [a] | Elemental analysis (%) [b] | | | | Conjugation efficiency (%) [c] | |
|---|---|---|---|---|---|---|
| | C | H | O | N | $^1$H NMR | Elemental analysis |
| 28,400 | 46.08 | 4.82 | 56.57 | 0.41 | 52.7 | 69.4 |

Referring to Table 2, below, the results demonstrate that the process yields a final block copolymer without impurities. Bromide (a) was calculated by ion chromatography. DMSO (b) and dichloromethane (b) were calculated by gas chromatography and $^1$H NMR. Water (c) was calculated by Karl Fisher analysis. ND=not detectable.

TABLE 2

| Impurities (ppm/gram) | | | Moisture (%) |
|---|---|---|---|
| Bromide [a] | DMSO [b] | Dichloromethane [b] | Water [c] |
| 625 | ND | ND | 0.95 |

Example 2

Process for synthesizing a block co-polymer of PLGA and PLL. A 5 gram PLGA-PLL scale reaction will be used as an example for explaining chemical and solvent volumes used in this process. This is a non-limiting example and the reaction scale can be adapted using the chemical and solvent volume examples provided.

Coupling Process steps. Coupling generally includes the use of N,N'-dicyclohexylcarbodiimide, distilled water, N-hydroxysuccinimide, and dimethyl sulfoxide. An example of coupling process steps follows: Two catalysts are added to the PLGA and PLL polymers and a conjugation reaction occurs. Dimethyl sulfoxide is added and the solution is filtered to remove by products. The solution is then dialyzed for using dialysis membranes and distilled water. The solution is then freeze dried to remove all water.

An example of coupling process steps follows:
1. 5 g+/−0.01 g of PLGA powder and 363 mg+/−0.5 mg of PLL were weighed and placed into the flask.
2. The following materials were added to this flask
   a. N,N'-Dicyclohexylcarbodiimide (DCC), weight: (50 mg+/−2.0 mg
   b. N-hydroxysuccinimide (NHS) weight: 28 mg+/−0.5 mg
3. Vacuum pressure was applied to this flask and dried for 30 minutes+/−1 minute.
4. The vacuum line on the vacuum manifold was shut off and the argon pressurized line was slowly opened.
   a. This removed the ambient air from the Schlenk flask and replaced it with Argon, creating an inert environment in the flask.
5. 25 mL of Dimethyl sulfoxide (DMSO) was added to the flask.
6. The plate stirrer was turned on to a set point of 320 rpm+/−20 rpm.
7. The solution was allowed to homogenize and was reacted at room temperature for 48 hours+/−2 hours on the plate stirrer.
8. After 48 hours, the rubber stopper was removed from the Schlenk flask and 25 ml of DMSO was added to the flask resulting in a polymer solution of 100 mg/ml.
9. The reacted solution was transferred into a 5 ml syringe body using a glass pipette.
10. The solution was filtered through a 0.22 μm filter into a 40 ml glass vial.
11. Steps 9 and 10 were repeated for the remaining solution volume.
a. This step was used to remove dicyclohexylurea (DCU) which is a byproduct of this reaction step.
12. The filtered solution was loaded into a Spectra/Por 4 Dialysis membrane (MWCO12-14,000) and both ends of the tube were clipped off.
13. The tube was placed into a 2 L glass beaker filled with approximately 1.5 L of distilled water and a magnetic stirrer.
14. The stir plate was turned on and the speed was set at 100 rpm+/−5 rpm and this process was run for 24 hours+1-10 minutes, the water was changed after the first 2 hours, and then the following 16 hours, 3 hours and 3 hours. This time structure allowed for overnight processing. Note: Once the above step is complete the solution was comprised of a separated powder and water mix.
15. The powder and water solution was transferred from the dialysis membrane into 50 ml falcon tubes.
16. It was ensured that the water level is high enough to cover the highest level of powder in the tube.
   a. If not, the needed amount of distilled water was added to the tube.
17. The top opening of the flask was covered with a KimWipe™ (VWR82003-820) and affixed with a rubber band (VWR 500024-262) around the top of the tube.
18. A dewar flask was filled with liquid nitrogen and the filled tubes were lowered into the dewar flask and allowed to freeze for 10 minutes+/−1 minute.
19. The tubes were removed and immediately placed in the glass flask on the Lyophilizer (freeze Dryer).
20. The lyophilizer was started and allowed to run for 48 hours+/−2 hours. This step was deemed complete when a dried white powder was observed.

De-protection Processing Steps. Deprotection generally includes the use of Hbr/acetic acid and Methylene chloride. The dry polymer is dissolved in methylene chloride. The solution is then rotary evaporated. The remaining solution is diluted with glacial acetic acid. An example of de-protection processing steps follows:
21. The dry powder was placed in a 250 ml round bottom flask and a magnetic stir bar was inserted.
22. 40 ml+1-1 ml of methylene chloride was added to the flask and the stir plate was turned on at 300 rpm+/−10 rpm for 30 minutes+/−2 minutes until the polymer was dissolved. The water bath was filled with distilled water and the bath setting temperature was turned to 27° C.+/−2° C. and the water bath was allowed to heat up to set temperature.
23. The flask was attached to the Buchi RotoVap and the following parameters were applied to the rotovap system:
   a. Rotation speed: 100 rpm+/−5 rpm; Vacuum Pressure: 250 mm Hg-100 mm Hg; Water Bath temperature: 25-29° C.
24. Once the water bath was ready, dry ice was loaded into the cold finger trap, ⅔ of the height, and filled with acetone up to the level of the dry ice.
25. The vacuum pump was turned on and set to 250 mm.
26. The rotation was turned on and set to 100 rpm+/−5 rpm.
27. The rotovap was run for 10 minutes+/−1 minute. The vacuum pressure was increased by 30 mm Hg every 2 minutes bringing the final vacuum pressure to 100 mm Hg in 10 minutes.
28. The rotovap was allowed to run at 100 mm Hg for 2 to 3 minutes.
   a. This process was complete once a thin clear polymer film was observed in the round bottom flask.
29. The round bottom flask was removed from the rotovap and placed in the fume hood.
30. 5 mL Hbr/acetic acid was added to dissolve the thin polymer film with a stir bar stirring at 300 rpm and yielded a cloudy yellow solution.
31. The top of the flask was covered with a rubber stopper and allowed to react for 90 minutes+/−5 minutes.
32. After 90 minutes, the flask was placed back onto the rotovap and steps 26 to 29 were repeated.
33. The cold finger trap was checked and dry ice and acetone were added if needed.
34. After rotovap drying, the solution became yellowish-orange in color and cloudy.
35. The solution was transferred to a 50 mL beaker. The solution was diluted with 10 mL of glacial acetic acid and mixed well.

Precipitation Processing steps. Precipitation processing generally includes the use of ethanol. The de-protected stock is place into a syringe body and injected into a beaker containing ethanol. The solution then solidifies in the ethanol. An example of precipitation processing steps follows:
36. A 2 L beaker was filled with 1.5 L of Ethanol and a stir bar was added.
37. The stir plate was turned on to a setting of 500 rpm+1-10 rpm.
38. The polymer solution was aspirated from the 50 mL beaker with a 5 mL syringe body with a 16.5 gauge needle.
39. The polymer solution was slowly injected into the ethanol.
40. The polymer solution solidified once it contacted the ethanol.
41. Once the polymer solution was injected out of the syringe, the polymer settled to the bottom of the beaker 2-3 minutes later.

Purification Processing Steps. Purification processing generally includes the use of sodium bicarbonate, distilled water, ethanol, dimethyl sulfoxide and dicholoromethane. The polymer is washed using sodium bicarbonate, distilled water and ethanol. Dichloromethane is added to the polymer and the dissolved solution is then rotary evaporated. Dimethyl sulfoxide is added to the polymer solution and then dialyzed using dialysis membranes for 24 hours. The solution is then rotary evaporated yielding the final dried product. An example of purification processing steps follows:

42. The ethanol was poured carefully through a Teflon™ sieve. The yellowish ethanol was completely drained with the polymer staying inside the sieve.
43. 500 ml of saturated sodium bicarbonate was prepared by mixing 500 ml of Distilled water and 40 g of sodium bicarbonate.
44. The 1 L beaker was filled with 500 mL of the saturated sodium bicarbonate solution and the solidified polymer was placed into this beaker.
45. Using a Teflon™ stirring rod, the solidified polymer was compressed and the stir plate was turned on and allowed to run for 10 minutes+/−30 seconds.
46. The sodium bicarbonate solution was drained into another flask and 500 mL of distilled water was added to the flask. It was allowed to run for 15 minutes+/−2 minutes with frequent compression and stirring with a PTFE stirring rod.
47. The distilled water was drained into another flask and 300 mL of ethanol was added to the flask and the polymer was allowed to soak in the ethanol for 15 minutes+/−2 minutes.
48. All Ethanol was fully drained from the flask.
49. The solidified polymer was transferred to a 40 mL vial and allowed to sit for 2 to 3 minutes.
50. Residual ethanol leached from the polymer. At this time the residual ethanol was removed by pouring it out of the beaker.
51. 30 mL+/−5 mL of dichloromethane was added to the 40 ml flask and dissolved the polymer.
52. The polymer solution was transferred to a clean 250 mL round bottomed flask.
53. The solution was rotovapped per steps 26-29.
54. The starting vacuum pressure was set to 200 mm Hg and the pressure was increased to 20 mm Hg in 10 minutes, and the pressure was increased by 20 mm Hg every minute to a final set point of 20 mm Hg.
55. The rotovap was run for 30 minutes at the final pressure of 20 mm Hg.
56. The round bottomed flask was removed from the rotovap and 40 mL+/−5 mL of dimethyl sulfoxide was added and the solution was transferred into Spectra/Por 4 Dialysis membrane (MWCO12-14,000), both ends with were clipped off with clips.
57. A 2 L beaker was filled with 1.5 L of distilled water and a magnetic stir bar was added.
58. The dialysis membrane was added to the water and the stirrer was turned on and the speed was set at 100 rpm+/−10 rpm.
59. Step 58 was run for 24 hours, changing the water every 3 hours.
60. If dialysis runs over night, it is preferable that the first water change occurs before end of day, the 2nd change preferably occurs at the beginning of the next day, and the 3rd and 4th water changes preferably occur 3 hours apart after the start of the second day.
61. The wet polymer was transferred into 50 ml falcon tubes.
62. Distilled water was added to the tubes, ensuring there enough water covered the highest level of powder in the tube.
63. The top opening of the flask was covered with a KimWipe™ (VWR82003-820) and affixed with a rubber band (VWR 500024-262) around the top of the tube.
64. A dewar flask was filled with liquid Nitrogen and the filled tubes were lowered into the dewar flask and allowed to freeze for 10 minutes+/−1 minute.
65. The tubes were removed and immediately placed in the glass flask on the Lyophilizer (freeze dryer).
66. The Lyophilizer was started and allowed to run for 48 hours+/−2 hours. This step is deemed complete when a dried white powder is observed, completing the process.

Examples above include specific numbered procedures and in some cases sub-procedures listed within a specific numbered procedure. Some of the procedures or sub-procedures described above may be specific routine laboratory practices that may be substituted with other suitable routine laboratory practices. A process herein includes any one or more of the numbered procedures or sub-procedures above, where the numbered procedures or sub-procedures selected are performed in any suitable order, and with any suitable solvent, reagent or condition.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of synthesizing a copolymer comprising:
coupling a degradable polymer to a poly(amino acid) containing protected side chains by combining the degradable polymer, the poly(amino acid), a solvent, and a coupling catalyst to form a copolymer solution having copolymer;
isolating the copolymer to form an isolated copolymer;
dissolving the isolated copolymer in a deprotecting solvent;
forming a thin film by removing at least a portion of the deprotecting solvent;
adding a deprotecting agent to the thin film to form a deprotected copolymer; and
isolating the deprotected copolymer, wherein isolating the deprotected copolymer includes precipitating the deprotected copolymer in ethanol or a mixture including ethanol.

2. The method of claim 1, wherein the deprotecting solvent is dichloromethane.

3. The method of claim 2, wherein the deprotecting agent is hydrogen bromide.

* * * * *

UNITED STATES PATENT AND TRADEMARK OFFICE
CERTIFICATE OF CORRECTION

PATENT NO. : 10,131,786 B2
APPLICATION NO. : 14/232525
DATED : November 20, 2018
INVENTOR(S) : Harvey et al.

Page 1 of 1

It is certified that error appears in the above-identified patent and that said Letters Patent is hereby corrected as shown below:

In the Specification

At Column 8/Line 60: "bock" should read --block--

At Column 9/Line 22: "14 gauge×6"" should read --14 gauge X6"--

At Column 9/Line 23: "16 gauge×6"" should read --16 gauge X6"--

At Column 11/Line 28: "14 gauge×6"" should read --14 gauge X6"--

At Column 11/Line 40: "a16" should read --a 16--

At Column 12/Line 43: "Impurities (ppm/gram)" should read --Impurities (ppm)--

At Column 13/Line 2: "5g+/-0.01g." should read --5g+/-0.1g.--

At Column 13/Line 42: "hours +1-10 minutes" should read --hours+/-10 minutes--

At Column 14/Line 30: "rotavap" should read --rotovap--

At Column 14/Line 45: "rotavap" should read --rotovap--

At Column 14/Line 52: "is place" should read --is placed--

At Column 14/Line 58: "rpm+1-10 rpm." should read --rpm+/-10 rpm.--

At Column 15/Line 55: "with were clipped" should read --were clipped--

Signed and Sealed this
Tenth Day of September, 2019

Andrei Iancu
*Director of the United States Patent and Trademark Office*